United States Patent
Mulier et al.

(10) Patent No.: US 6,706,039 B2
(45) Date of Patent: *Mar. 16, 2004

(54) METHOD AND APPARATUS FOR CREATING A BI-POLAR VIRTUAL ELECTRODE USED FOR THE ABLATION OF TISSUE

(75) Inventors: Peter M. J. Mulier, Stillwater, MN (US); Michael F. Hoey, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/865,591

(22) Filed: May 25, 2001

(65) Prior Publication Data

US 2001/0025178 A1 Sep. 27, 2001

Related U.S. Application Data

(63) Continuation of application No. 09/347,971, filed on Jul. 6, 1999, now Pat. No. 6,238,393.
(60) Provisional application No. 60/091,929, filed on Jul. 7, 1998.

(51) Int. Cl.[7] ................................................ A61B 18/14
(52) U.S. Cl. ............................ 606/41; 606/48; 606/50; 607/99; 607/105; 607/113
(58) Field of Search ..................... 606/41, 48, 50; 604/114; 607/99, 105, 113

(56) References Cited

U.S. PATENT DOCUMENTS

| | | | |
|---|---|---|---|
| 4,976,711 A | * 12/1990 | Parins et al. | 606/48 |
| 5,458,596 A | * 10/1995 | Lax et al. | 606/41 |
| 5,458,597 A | 10/1995 | Edwards et al. | |
| 5,536,267 A | 7/1996 | Edwards et al. | |
| 5,683,384 A | 11/1997 | Gough et al. | |
| 5,697,536 A | * 12/1997 | Eggers et al. | 604/114 |
| 5,860,974 A | * 1/1999 | Abele | 606/41 |
| 6,071,280 A | 6/2000 | Edwards et al. | |
| 6,179,824 B1 | * 1/2001 | Eggers et al. | 604/28 |
| 6,238,393 B1 | * 5/2001 | Mulier et al. | 606/41 |
| 6,327,505 B1 | * 12/2001 | Medhkour et al. | 604/114 |

* cited by examiner

*Primary Examiner*—Lee Cohen
(74) *Attorney, Agent, or Firm*—Daniel W. Latham; Timothy A. Czaja

(57) ABSTRACT

A method and apparatus for creating a virtual electrode to ablate bodily tissue. The apparatus includes an outer tube, a first electrode, an inner tube and a second electrode. The outer tube is fluidly connected to a source of conductive fluid and defines a proximal end and a distal end. The distal end includes an opening for delivering conductive fluid from the outer tube. The first electrode is disposed at the distal end of the outer tube for applying a current to conductive fluid delivered from the outer tube. The inner tube is coaxially received within the outer tube and is connected to a source of conductive fluid. The inner tube defines a proximal end and a distal end, with the distal end forming an opening for delivering conductive fluid from the inner tube. Finally, the second electrode is disposed at the distal end of the inner tube for applying a current to conductive fluid delivered from the inner tube. With this configuration, upon final assembly, the distal end of the outer tube is axially spaced from the distal end of the inner tube such that the first electrode is spaced from the second electrode. As a result, a bi-polar virtual electrode can be established.

24 Claims, 3 Drawing Sheets

METHOD AND APPARATUS FOR CREATING A BI-POLAR VIRTUAL ELECTRODE USED FOR THE ABLATION OF TISSUE

CROSS-REFERENCE TO RELATED APPLICATIONS

This application is a continuation of U.S. patent application Ser. No. 09/347,971, entitled "Method and Apparatus for Creating a Bi-Polar Virtual Electrode Used for the Ablation of Tissue" filed on Jul. 6, 1999, now U.S. Pat. No. 6,238,393. In addition, this application claims the benefit of U.S. Provisional Application No. 60/091,929, filed on Jul. 7, 1998.

FIELD OF THE INVENTION

The present invention relates generally to an apparatus for creating a virtual electrode. More particularly, the present invention relates to an apparatus for the creation of a virtual electrode that is useful for the ablation of soft tissue and neoplasms.

BACKGROUND OF THE PRESENT INVENTION

The utilization of an electric current to produce an ameliorative effect on a bodily tissue has a long history, reportedly extending back to the ancient Greeks. The effects on bodily tissue from an applied electric current, and thus the dividing line between harmful and curative effects, will vary depending upon the voltage levels, current levels, the length of time the current is applied, and the tissue involved. One such effect resulting from the passage of an electric current through tissue is heat generation.

Body tissue, like all non-superconducting materials, conducts current with some degree of resistance. This resistance creates localized heating of the tissue through which the current is being conducted. The amount of heat generated will vary with the power P deposited in the tissue, which is a function of the product of the square of the current I and the resistance R of the tissue to the passage of the current through it ($P=I^2R$.).

As current is applied to tissue, then, heat is generated due to the inherent resistance of the tissue. Deleterious effects in the cells making up the tissue begin to occur at about 42° Celsius. As the temperature of the tissue increases due to heat generated by the tissue☐s resistance, the tissue will undergo profound changes and eventually, as the temperature becomes high enough, that is, generally greater than 45° C., the cells will die. The zone of cell death is known as a lesion and the procedure followed to create the lesion is commonly called an ablation. As the temperature increases beyond cell death temperature, complete disintegration of the cell walls and cells caused by boiling off of the tissue's water can occur. Cell death temperatures can vary somewhat with the type of tissue to which the power is being applied, but generally will begin to occur within the range of 45° to 60° C., though actual cell death of certain tissue cells may occur at a higher temperature.

In recent times, electric current has found advantageous use in surgery, with the development of a variety of surgical instruments for cutting tissue or for coagulating blood. Still more recently, the use of alternating electric current to ablate, that is, kill, various tissues has been explored. Typically, current having a frequency from about 3 kilohertz to about 300 gigahertz, which is generally known as radiofrequency or radiofrequency (RF) current, is used for this procedure. Destruction, that is, killing, of tissue using an RF current is commonly known as radiofrequency ablation. Often radiofrequency ablation is performed as a minimally invasive procedure and is thus known as radiofrequency catheter ablation because the procedure is performed through and with the use of a catheter. By way of example, radiofrequency catheter ablation has been used to ablate cardiac tissue responsible for irregular heartbeats or arrythmias.

The prior art applications of current to tissue have typically involved applying the current using a dry electrode. That is, a metal electrode is applied to the tissue desired to be affected and a generated electric current is passed through the electrode to the tissue. A commonly known example of an instrument having such an operating characteristic is an electrosurgical instrument known as a bovie knife. This instrument includes a cutting/coagulating blade electrically attached to a current generator. The blade is applied to the tissue of a patient and the current passes through the blade into the tissue and through the patients body to a metal base electrode or ground plate usually placed underneath and in electrical contact with the patient. The base electrode is in turn electrically connected to the current generator so as to provide a complete circuit.

As the current from the bovie knife passes from the blade into the tissue, the resistance provided by the tissue creates heat. In the cutting mode, a sufficient application of power through the bovie knife to the tissue causes the fluid within the cell to turn to steam, creating a sufficient overpressure so as to burst the cell walls. The cells then dry up, desiccate, and carbonize, resulting in localized shrinking and an opening in the tissue. Alternatively, the bovie knife can be applied to bleeding vessels to heat and coagulate the blood flowing therefrom and thus stop the bleeding.

As previously noted, another use for electrical instruments in the treatment of the body is in the ablation of tissue. To expand further on the brief description given earlier of the ablation of cardiac tissue, it has long been known that a certain kind of heart tissue known as sino-atrial and atrio-ventricular nodes spontaneously generate an electrical signal that is propagated throughout the heart along conductive pathways to cause it to beat. Occasionally, certain heart tissue will misfire, causing the heart to beat irregularly. If the errant electrical pathways can be determined, the tissue pathways can be ablated and the irregular heartbeat remedied. In such a procedure, an electrode is placed via a catheter into contact with the tissue and then current is applied to the tissue via the electrode from a generator of RF current. The applied current will cause the tissue in contact with the electrode to heat. Power will continue to be applied until the tissue reaches a temperature where the heart tissue dies, thereby destroying the errant electrical pathway and the cause of the irregular heartbeat.

Another procedure using RF ablation is transurethral needle ablation, or TUNA, which is used to create a lesion in the prostate gland for the treatment of benign prostatic hypertrophy (BPH) or the enlargement of the prostate gland. In a TUNA procedure, a needle having an exposed conductive tip is inserted into the prostate gland and current is applied to the prostate gland via the needle. As noted previously, the tissue of the prostate gland heats locally surrounding the needle tip as the current passes from the needle to the base electrode.

A lesion is created as the tissue heats and the destroyed cells may be reabsorbed by the body, infiltrated with scar tissue, or just become non-functional.

While there are advantages and uses for such dry electrode instruments, there are also several notable disadvantages. One of these disadvantages is that during a procedure, coagulum—dried blood cells and tissue cells—will form on the electrode engaging the tissue. Coagulum acts as an insulator and effectively functions to prevent current transfer from the blade to the tissue. This coagulum insulation can be overcome with more voltage so as to keep the current flowing, but only at the risk of arcing and injuring the patient. Thus, during surgery when the tissue is cut with an electrosurgical scalpel, a build-up of coagulated blood and desiccated tissue will occur on the blade, requiring the blade to be cleaned before further use. Typically, cleaning an electrode/scalpel used in this manner will involve simply scraping the dried tissue from the electrode/scalpel by rubbing the scalpel across an abrasive pad to remove the coagulum. This is a tedious procedure for the surgeon and the operating staff since it requires the real work of the surgery to be discontinued while the cleaning operation occurs. This procedure can be avoided with the use of specially coated blades that resist the build up of coagulum. Such specialty blades are costly, however.

A second disadvantage of the dry electrode approach is that the electrical heating of the tissue creates smoke that is now known to include cancer-causing agents. Thus, preferred uses of such equipment will include appropriate ventilation systems, which can themselves become quite elaborate and quite expensive.

A further, and perhaps the most significant, disadvantage of dry electrode electrosurgical tools is revealed during cardiac ablation procedures. During such a procedure, an electrode that is otherwise insulated but having an exposed, current carrying tip is inserted into the heart chamber and brought into contact with the inner or endocardial side of the heart wall where the ablation is to occur. The current is initiated and passes from the current generator to the needle tip electrode and from there into the tissue so that a lesion is created. Typically, however, the lesion created by a single insertion is insufficient to cure the irregular heartbeat because the lesion created is of an insufficient size to destroy the errant electrical pathway. Thus, multiple needle insertions and multiple current applications are almost always required to ablate the errant cardiac pathway, prolonging the surgery and thus increasing the potential risk to the patient.

This foregoing problem is also present in TUNA procedures, which similarly require multiple insertions of the needle electrode into the prostate gland. Failing to do so will result in the failure to create a lesion of sufficient size otherwise required for beneficial results. As with radiofrequency catheter ablation of cardiac tissue, then, the ability to create a lesion of the necessary size to alleviate BPH symptoms is limited and thus requires multiple insertions of the electrode into the prostate.

A typical lesion created with a dry electrode using RF current and a single insertion will normally not exceed one centimeter in diameter. This small size—often too small to be of much or any therapeutic benefit—stems from the fact that the tissue surrounding the needle electrode tends to desiccate as the temperature of the tissue increases, leading to the creation of a high resistance to the further passage of current from the needle electrode into the tissue, all as previously noted with regard to the formation of coagulum on an electrosurgical scalpel. This high resistance—more properly termed impedance since typically an alternating current is being used—between the needle electrode and the base electrode is commonly measured by the RF current generator. When the measured impedance reaches a predetermined level, the generator will discontinue current generation. Discontinuance of the ablation procedure under these circumstances is necessary to avoid injury to the patient.

Thus, a typical procedure with a dry electrode may involve placing the needle electrode at a first desired location; energizing the electrode to ablate the tissue; continue applying current until the generator measures a high impedance and shuts down; moving the needle to a new location closely adjacent to the first location; and applying current again to the tissue through the needle electrode. This cycle of electrode placement, electrode energization, generator shut down, electrode re-emplacement, and electrode re-energization, will be continued until a lesion of the desired size has been created. As noted, this increases the length of the procedure for the patient. Additionally, multiple insertions increases the risk of at least one of the placements being in the wrong location and, consequently, the risk that healthy tissue may be undesirably affected while diseased tissue may be left untreated. The traditional RF ablation procedure of using a dry ablation therefore includes several patient risk factors that both patient and physician would prefer to reduce or eliminate.

The therapeutic advantages of RF current could be increased if a larger lesion could be created safely with a single positioning of the current-supplying electrode. A single positioning would allow the procedure to be carried out more expeditiously and more efficiently, reducing the time involved in the procedure. Larger lesions can be created in at least two ways. First, simply continuing to apply current to the patient with sufficiently increasing voltage to overcome the impedance rises will create a larger lesion, though almost always with undesirable results to the patient. Second, a larger lesion can be created if the current density, that is, the applied electrical energy, could be spread more efficiently throughout a larger volume of tissue. Spreading the current density over a larger tissue volume would correspondingly cause a larger volume of tissue to heat in the first instance. That is, by spreading the applied power throughout a larger tissue volume, the tissue would heat more uniformly over a larger volume, which would help to reduce the likelihood of generator shutdown due to high impedance conditions. The applied power, then, will cause the larger volume of tissue to be ablated safely, efficiently, and quickly.

Research conducted under the auspices of the assignee of the present invention has focused on spreading the current density throughout a larger tissue volume through the creation, maintenance, and control of a virtual electrode within or adjacent to the tissue to be ablated. A virtual electrode can be created by the introduction of a conductive fluid, such as isotonic or hypertonic saline, into or onto the tissue to be ablated. The conductive fluid will facilitate the spread of the current density substantially equally throughout the extent of the flow of the conductive fluid, thus creating an electrode—a virtual electrode—substantially equal in extent to the size of the delivered conductive fluid. RF current can then be passed through the virtual electrode into the tissue.

A virtual electrode can be substantially larger in volume than the needle tip electrode typically used in RF interstitial ablation procedures and thus can create a larger lesion than can a dry, needle tip electrode. That is, the virtual electrode spreads or conducts the RF current density outward from the RF current source—such as a current carrying needle, forceps or other current delivery device—into or onto a larger volume of tissue than is possible with instruments that rely on the use of a dry electrode. Stated otherwise, the creation of the virtual electrode enables the current to flow with reduced resistance or impedance throughout a larger volume of tissue, thus spreading the resistive heating created by the current flow through a larger volume of tissue and thereby creating a larger lesion than could otherwise be created with a dry electrode.

While the efficacy of RF current ablation techniques using a virtual electrode has been demonstrated in several studies, the currently available instruments useful in such procedures lags behind the research into and development of hoped-for useful treatment modalities for the ablation of soft tissue and malignancies.

It would be desirable to have an apparatus capable of creating a virtual electrode for the controlled application of tissue ablating RF electric current to a tissue of interest so as to produce a lesion of desired size and configuration.

SUMMARY OF THE INVENTION

One aspect of the present invention provides a surgical apparatus for creating a virtual electrode to ablate bodily tissue. The surgical apparatus comprises an outer tube, a first electrode, an inner tube and a second electrode. The outer tube is fluidly connected to a source of conductive fluid and defines a proximal end and a distal end. In this regard, the distal end of the outer tube includes an opening for delivering a conductive fluid from the outer tube. The first electrode is disposed at the distal end of the outer tube and is configured to apply a current to conductive fluid delivered from the outer tube. The inner tube is coaxially received within the outer tube. The inner tube is fluidly connected to a source of conductive fluid and defines a proximal end and a distal end. In this regard, the distal end of the inner tube forms an opening for delivering a conductive fluid from the inner tube. The second electrode is disposed at the distal end of the inner tube. The second electrode is configured to apply a current to conductive fluid delivered from the inner tube. Upon final assembly, the distal end of the outer tube is axially spaced from the distal end of the inner tube such that the first electrode is spaced from the second electrode. With this configuration, then, a bi-polar virtual electrode can be established.

Another aspect of the present invention provides a surgical system for creating a virtual electrode to ablate bodily tissue. The surgical system includes a fluid source, a current source, and a surgical instrument. The fluid source maintains a supply of conductive fluid. The current source is configured to selectively supply an electrical current. The surgical instrument includes an outer tube, a first electrode, an inner tube and a second electrode. The outer tube is fluidly connected to the fluid source and defines a proximal end and a distal end. The distal end of the outer tube includes an opening for delivering the conductive fluid. The first electrode is disposed at the distal end of the outer tube and is electrically connected to the current source. The inner tube is coaxially received within the outer tube and is fluidly connected to the fluid source. The inner tube defines a proximal end and a distal end, with the distal end of the inner tube forming an opening for delivering the conductive fluid. The second electrode is disposed at the distal end of the inner tube and is electrically connected to the current source. Upon final assembly, the distal end of the outer tube is spaced from the distal end of the inner tube such that the conductive fluid is delivered as a first bolus from the outer tube and a second bolus from the inner tube. Current is applied to the first and second boluses by the first and second electrodes, respectively. With this configuration, a bi-polar virtual electrode can be created.

Another aspect of the present invention relates to a method for ablating bodily tissue at a target site. The method includes delivering a first bolus of a conductive fluid at the target site. A second bolus of conductive fluid is also delivered at the target site, the second bolus being spaced from the first bolus. Finally, a current is substantially simultaneously applied to each of the first bolus and the second bolus to create a virtual electrode, ablating tissue in contact with the first and second boluses. In one preferred embodiment, tissue between the first and second boluses is collapsed prior to applying the current.

DETAILED DESCRIPTION OF THE PREFERRED EMBODIMENTS

Figure 1:
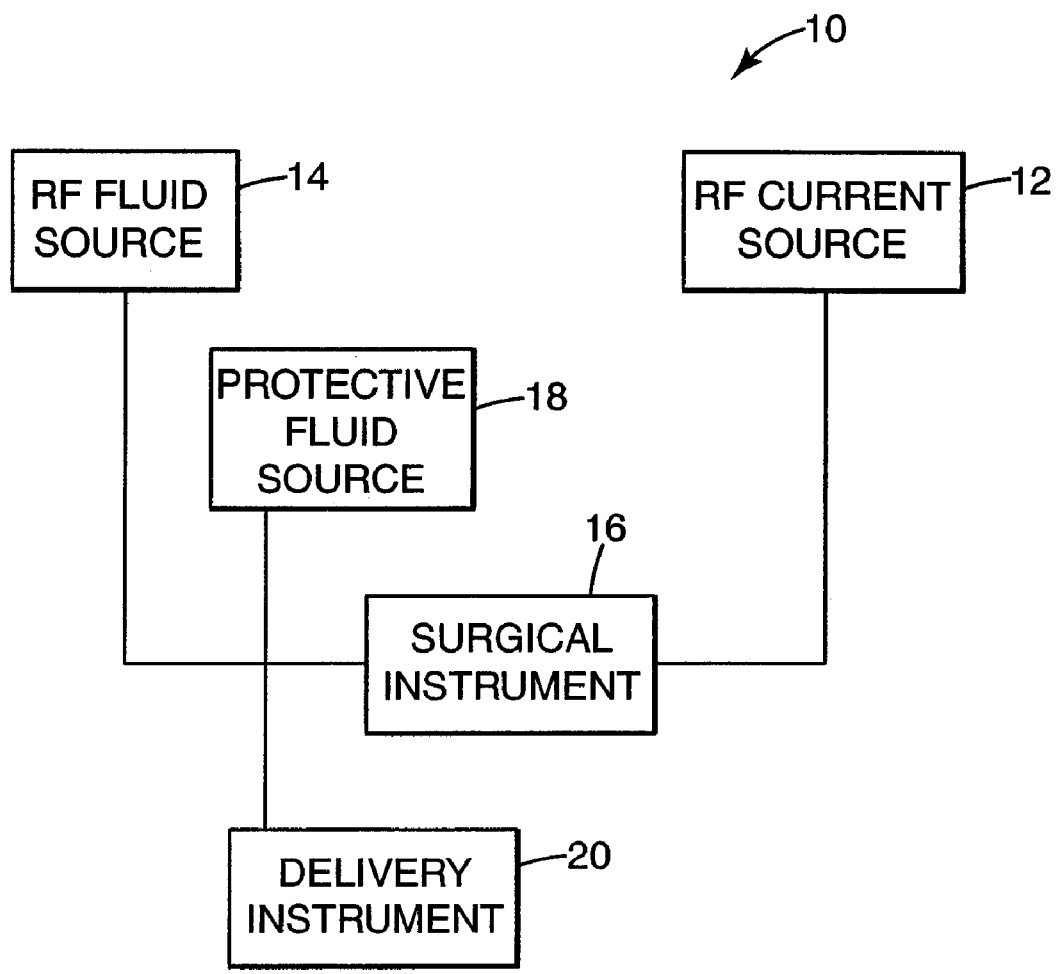
FIG. 1 is a block diagram of a system for creating a virtual electrode in accordance with the present invention.

FIG. 1 illustrates in block form a system 10 for RF ablation useful with the present invention. The system 10 includes a current source of radiofrequency alternating electric current 12, a fluid source of RF ablating fluid 14, including but not limited to saline and other conductive solutions, and a surgical instrument 16 for delivering RF current and ablation fluid to a tissue site (not shown) for ablation purposes. In one preferred embodiment, the surgical instrument 16 is connected to the current source 12 and the fluid source 14. It will be understood that the current source 12 and the fluid source 14 may be combined into a single operational structure controlled by an appropriate microprocessor for a controlled delivery of ablating fluid and a controlled application of RF current, both based upon measured parameters such as but not limited to, flow rate, tissue temperature at the ablation site and at areas surrounding the ablation site, impedance, the rate of change of the impedance, the detection of arcing between the surgical instrument and the tissue, the time period during which the ablation procedure has been operating, and additional factors as desired.

While the surgical instrument 16 is shown as being connected to both the current source 12 and the fluid source 14, the present system is not so limited but could include separate needles or other instruments useful in RF liquid ablation procedures, that is, for example, a single straight or coiled needle having an exposed end and a fluid flow path there through could be used to deliver both fluid and current to the target tissue for ablation purposes. Alternatively, a separate needle could be used to deliver the current and a separate needle or needles could be used to deliver fluid to the target tissue. In addition, the application of the present system is not limited to the use of straight needles or helical needles as surgical instruments but could find use with any type of instrument wherein a conductive solution is delivered to a tissue and an RF current is applied to the tissue through the conductive fluid. Such instruments thus would include straight needles, helical needles, forceps, roller balls, instruments for the treatment of vascular disorders, and any other instrument.

In one preferred embodiment, the system 10 further includes a second fluid source 18 for delivery of tissue protecting fluid, via a delivery instrument 20, to a tissue whose ablation is not desired.

Figure 2:
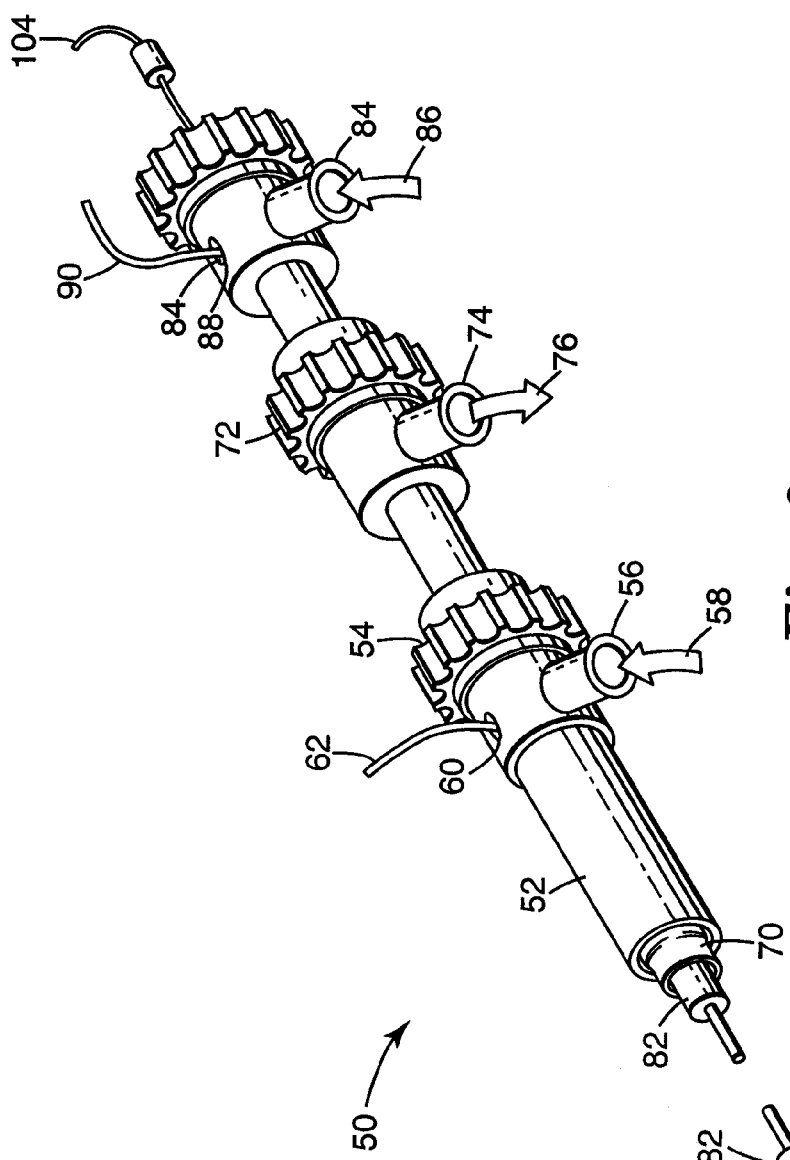
FIG. 2 is a perspective view, with a portion cut away, of a surgical apparatus in accordance with the present invention.
Figure 2:
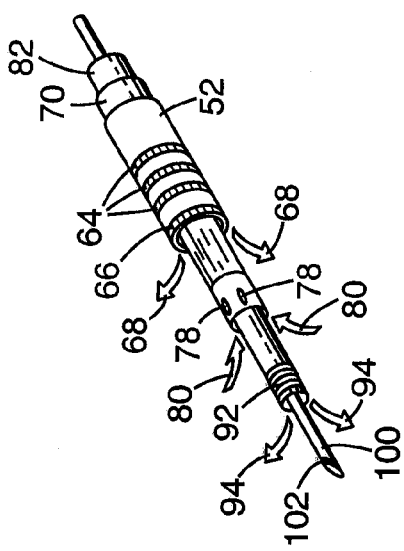

The surgical instrument 16 may assume a wide variety of forms. One preferred embodiment of a surgical apparatus 50 is shown in FIG. 2. The apparatus 50 generally includes a bi-polar electrode that is useful in an ablation procedure using an RF ablating fluid such as, but not limited to, isotonic or hypertonic saline. Further, the apparatus 50 generally includes a plurality of coaxial thin walled tubes forming a catheter delivery system for RF ablating fluid and RF ablating current. Thus, the apparatus 50 preferably includes a first or outer thin walled tube 52 having a proximally attached hemostasis valve 54. The valve 54 includes an inlet 56 for RF ablating fluid flow as indicated by arrow 58 and also an access port 60 for an electrical line 62, which can be electrically connected to the RF current source 12 (FIG. 1). A distal end of the first tube 52 may be provided with one or more thermocouples or other temperature sensors 64. The distal end of the first tube 52 also includes an electrode 66 which is electrically connected to the line 62, thereby providing one of the two bi-polar electrodes envisioned by a preferred embodiment of the present invention. It will be understood that the first tube 52 is electrically insulated or otherwise non-conductive. The first tube 52 provides a flow passage for the RF ablating fluid from the fluid source 14 (FIG. 1) to the distal end of the first tube 52 where it exits the first tube 52 as indicated by arrows 68.

The apparatus 50 further includes a second or intermediate thin walled tube 70 coaxially disposed within the first tube 52. The second tube 70 has a proximally attached hemostasis valve 72. The valve 72 includes a suction port 74 for directing fluid flow as indicated by arrow 76. A distal end of the second tube 70 may be provided with one or more vacuum apertures 78 through which a suction is applied to surrounding tissue (not shown), via a vacuum formed at the suction port 74. Thus, applying suction to the suction port 74 will draw the surrounding tissue into contact with the vacuum apertures 78 and the distal end of the second tube 70. In addition, with this same process, some RF ablating fluid may be removed via the applied suction as indicated by arrows 80.

The apparatus 50 further includes a third or inner thin walled tube 82 coaxially disposed within the second tube 70. The third tube 82 has a proximally attached hemostasis valve 84. The valve 84 includes an inlet 84 for RF ablating fluid flow as indicated by arrow 86 and also an access port 88 for an electrical line 90, which can be electrically connected to the current source 12 (FIG. 1). A distal end of the third tube 82 also includes an electrode 92, which is electrically connected to the line 90, thereby providing the other one of the two bi-polar electrodes envisioned by a preferred embodiment of the present invention. It will be understood that the third tube 82 is electrically insulated or otherwise non-conductive. The third tube 82 provides a flow passage for the RF ablating fluid from the fluid source 14 (FIG. 1) to the distal end of the third tube 82 where it exits the third tube 82 as indicated by arrows 94.

The surgical apparatus 50 may further include a probe 100 that extends through an interior passage of the third tube 82 and that is freely movable therewithin. The probe 100 may include a thermocouple 102 disposed at a most distal end thereof and may be connected via an electrical line 104 to the RF current source 12 (FIG. 1) to provide a temperature measurement at a predetermined distance from the electrodes 66 and 92.

In operation, following delivery to a particular target site, RF ablating fluid will be provided to the ports 56 and 84 from the fluid source 14 (FIG. 1). The fluid will exit the distal ends of the first tube 52 and the third tube 82, respectively, and begin to form boluses of fluid along or within the tissue at the target site. Application of a suction at the vacuum aperture 78, via the suction port 74, will cause the tissue surrounding the distal end of the second tube 70 to be collapsed or pulled into a substantially fluid tight relationship with the second tube 70, thereby preventing migration of the fluid, in particular via a capillary effect, along the second tube 70 between the distal ends of the first and third tubes 52, 82. RF ablating power can be applied and an ablation procedure can be carried out. By the application of suction to the tissue and the prevention of the flow of fluid along the second tube 70, shorting of the current between the electrodes 66 and 92 can be avoided.

Figure 3:
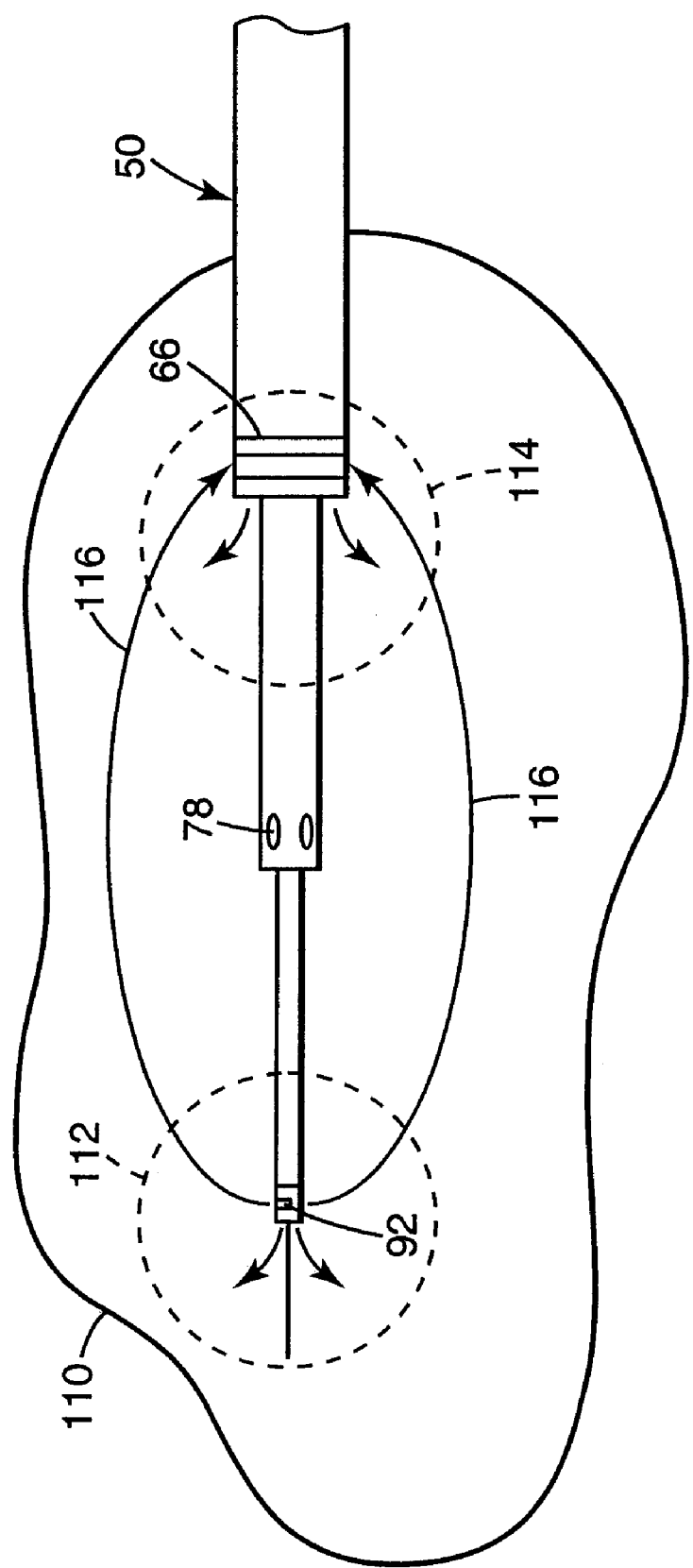
FIG. 3 is a schematic view of a portion of the surgical apparatus of FIG. 2 ablating bodily tissue.

FIG. 3 represents schematically the fluid flow and current flow achieved during use of the present invention. Thus, FIG. 3 shows a tissue 110, such as liver, into which a portion of the surgical apparatus 50 has been inserted. Infusion of the RF ablating fluid will initially create two separate boluses of fluid, 112 and 114. If not for the suction applied to the tissue surrounding vacuum apertures 78, fluid would tend to travel along the path created during insertion and placement of the apparatus 50 in the tissue 110. Applying suction intermediate the release of the fluid, however, prevents such fluid travel and substantially prevents any shortage between the electrodes 66, 92 directly therebetween. The applied current can thus spread readily through the boluses 112, 114 and then travel therebetween as indicated by the lines 116. In this way, then, ablation can be accomplished between the bi-polar electrodes 66 and 92. The lesion created with the use of such a bi-polar structure will essentially be the size of the boluses 112, 114 at a minimum, though it will be understood that cell-to-cell thermal conduction will occur that will make the lesion in reality larger than the boluses 112, 114, assuming that power is left on for the appropriate length of time.

As is well known, when an electro-surgical tool is used, or for that matter, any electrical device, a complete circuit for current flow must be provided. Thus, when a monopolar surgical instrument such as a bovie knife is used, a ground pad connected to the RF current generator is placed under the patient to provide a complete electrical circuit from the generator, to the knife, through the patient to the ground pad, and back to the generator. With the present invention, no ground pad is needed. The current flows from the current source 12 (FIG. 1) to one of the two electrodes 66 or 92 on the apparatus 50, through the patient to the other electrode 66 or 92, and then back to the current source 12. Such bi-polar structure enables the physician to localize the effect of the current passing through the patient, thereby avoiding certain risks associated with the use of a monopolar device, including but not limited to the risk of burns where the ground pad contacts the patient. Additionally, by controlling the relative spacing between the two electrodes 66, 92 of a bi-polar instrument, the size of the lesion can be controlled. Thus, where the electrodes 66, 92 are close to each other, there will be little tissue between them through which the current will travel and the lesion size will be reduced relative to an instrument where the electrodes are spaced relatively farther apart. In addition, the shape of the lesion is somewhat controllable by controlling both the fluid flow and the spacing of the electrodes 66, 92. It will be understood that regardless of the device used that the lesion size and shape is a product of many factors, including the tissue composition, the conductivity of the fluid, the amount of applied current, the amount of cell-to-cell thermal conductivity, the time period the current is applied, tissue temperature, and fluid temperature when applied, among others.

Although the present invention has been described with reference to preferred embodiments, workers skilled in the art will recognize that changes may be made in form and detail without departing from the spirit and scope of the invention.

What is claimed is:

1. A method for the treatment of tissue, the method comprising:

providing a tissue;

providing an electric current;

providing an electrically conductive fluid;

providing an apparatus for the treatment of the tissue, the apparatus configured to dispense the electrically conductive fluid to the tissue and apply the electric current to the tissue through the conductive fluid, the apparatus comprising:
- a bipolar electrode configuration comprising a first electrode spaced from a second electrode, the first electrode and the second electrode both uncovered and configured to be exposed to and adjacent to the tissue;
- the first electrode located at the distal end of a first tube, the first tube providing a first tube flow passage and a first tube flow passage opening, the first tube flow passage opening positioned to dispense the electrically conductive fluid adjacent the first electrode; and
- the second electrode located at the distal end of a second tube, the second tube providing a second tube flow passage and a second tube flow passage opening, the second tube flow passage opening positioned to dispense the electrically conductive fluid adjacent the second electrode;

positioning the first electrode adjacent to the tissue;

positioning the second electrode adjacent to the tissue;

dispensing the electrically conductive fluid from the first tube flow passage opening adjacent the first electrode and from the second tube flow passage opening adjacent the second electrode;

providing the electric current to the first electrode and to the second electrode; and applying the electric current from the first electrode and the second electrode to the tissue located adjacent the first electrode and to the tissue located adjacent the second electrode, and to the conductive fluid dispensed adjacent the first electrode and the conductive fluid dispensed adjacent the second electrode, respectively.

2. The method of claim 1 further comprising:

arranging the first fluid passage opening and the second fluid passage opening to facilitate a reduction in fluid interaction between the electrically conductive fluid dispensed from the first and second tube flow passage openings, respectively, external the apparatus.

3. The method of claim 1 further comprising:

creating a first virtual electrode with the electrically conductive fluid adjacent the first electrode;

creating a second virtual electrode with the electrically conductive fluid adjacent the second electrode.

4. The method of claim 3 further comprising:

arranging the first virtual electrode from the second virtual electrode to reduce interaction between the electrically conductive fluid dispensed from the first and second tube flow passage openings, respectively, external the apparatus.

5. An apparatus to treat tissue in the presence of an electrical current and an electrically conductive fluid, the apparatus comprising:

a bipolar electrode configuration comprising a first electrode spaced from a second electrode, the first electrode and the second electrode both uncovered and configured to be exposed to and adjacent to the tissue;

the first electrode located at the distal end of a first tube, the first tube providing a first tube flow passage and a first tube flow passage opening, the first tube flow passage opening positioned to dispense the electrically conductive fluid adjacent the first electrode;

the second electrode located at the distal end of a second tube, the second tube providing a second tube flow passage and a second tube flow passage opening, the second tube flow passage opening positioned to dispense the electrically conductive fluid adjacent the second electrode; and wherein the first fluid passage opening and the second fluid passage opening are arranged to facilitate a reduction in fluid interaction between the electrically conductive fluid dispensed from the first and second tube flow passage openings, respectively, external the apparatus.

6. The apparatus of claim 5, further comprising:

a vacuum tube located between the first tube and the second tube.

7. An apparatus to treat tissue in the presence of an electrical current and an electrically conductive fluid, the apparatus comprising:

a bipolar electrode configuration comprising a first electrode spaced from a second electrode, the first electrode and the second electrode both uncovered and configured to be exposed to and adjacent to the tissue;

the first electrode located at the distal end of a first tube, the first tube providing a first tube flow passage and a first tube flow passage opening, the first tube flow passage opening positioned to dispense the electrically conductive fluid adjacent the first electrode; and the second electrode located at the distal end of a second tube, the second tube providing a second tube flow passage and a second tube flow passage opening, the second tube flow passage opening positioned to dispense the electrically conductive fluid adjacent the second electrode;

a separation device, at least a portion of which is disposed between the first tube flow passage opening and the second tube flow passage opening; and wherein the separation device facilitates a reduction in fluid interaction between the electrically conductive fluid dispensed from the first and second tube flow passage openings, respectively, external the apparatus.

8. The apparatus of claim 7, wherein:

the separation device comprises a vacuum tube.

9. The method of claim 8 wherein:

the electrically conductive solution comprises saline.

10. An apparatus to treat tissue in the presence of an electrical current and an electrically conductive fluid, the apparatus comprising:

a bipolar electrode configuration comprising a first electrode spaced from a second electrode, the first electrode and the second electrode both uncovered and configured to be exposed to and adjacent to the tissue;

the first electrode located at the distal end of a first tube, the first tube providing a first tube flow passage and a first tube flow passage opening, the first tube flow passage opening positioned to dispense the electrically conductive fluid adjacent the first electrode; and the second electrode located at the distal end of a second tube, the second tube providing a second tube flow passage and a second tube flow passage opening, the second tube flow passage opening positioned to dispense the electrically conductive fluid adjacent the second electrode;

a separation device, at least a portion of which is disposed between the first tube flow passage opening and the second tube flow passage opening; and wherein the separation device facilitates a reduction in fluid interaction between the electrically conductive fluid dispensed from the first and second tube flow passage openings, respectively, external the apparatus.

11. The apparatus of claim 10, further comprising:

a vacuum tube located between the first tube and the second tube.

12. The apparatus of claim 10 wherein:

the first and the second tube are coaxially arranged; and the distal end of the first tube is axially spaced from the distal end of the second tube.

13. The apparatus of claim 10 wherein:

the first tube is at least one of electrically insulated and electrically non-conductive.

14. The apparatus of claim 10 wherein:

the second tube is at least one of electrically insulated and electrically non-conductive.

15. The apparatus of claim 10 further comprising:

a separation device to facilitate a reduction in fluid interaction between the electrically
  conductive fluid dispensed from the from the first and second tube flow passage
  openings, respectivley, external the apparatus.

16. The apparatus of claim 10 further comprising:

a separation device to prevent electrically conductive fluid dispensed from the first and
  second tube flow passage openings from the shorting electrical current directly between the electrodes.

17. The apparatus of claim 10 further comprising:

a separation device to prevent the migration of electrically conductive fluid dispensed
  from the first and second tube flow passage openings directly between the electrodes.

18. An apparatus to treat tissue in the presence of an electrical current and an electrically conductive fluid, the apparatus comprising:

a bipolar electrode configuration comprising a first electrode spaced from a second electrode, the first electrode and the second electrode both uncovered and configured to be exposed to and adjacent to the tissue;

the first electrode located at the distal end of a first tube, the first tube providing a first tube flow passage and a first tube flow passage opening, the first tube flow passage opening positioned to dispense the electrically conductive fluid adjacent the first electrode; and the second electrode located at the distal end of a second tube, the second tube providing a second tube flow passage and a second tube flow passage opening, the second tube flow passage opening positioned to dispense the electrically conductive fluid adjacent the second electrode;

a separation device, at least a portion of which is disposed between the first tube flow passage opening and the second tube flow passage opening; and wherein the separation device facilitates a reduction in fluid interaction between the electrically conductive fluid dispensed from the first and second tube flow passage openings, respectively, external the apparatus.

19. The apparatus of claim 18 wherein:

the separation device comprises a vacuum tube.

20. The apparatus of claim 18 wherein:

the first and the second tube are coaxially arranged; and the distal end of the first tube is axially spaced from the distal end of the second tube.

21. The apparatus of claim 18 wherein:

the first tube is at least one of electrically insulated and electrically non-conductive.

22. The apparatus of claim 18 wherein: the second tube is at least one of electrically insulated and electrically non-conductive.

23. The apparatus of claim 18 wherein:

the separation device prevents electrically conductive fluid dispensed from the first and
  second tube flow passage openings from shorting electrical current directly between the electrodes.

24. The apparatus of claim 18 wherein:

the separation device prevents the migration of electrically conductive fluid dispensed
  from the first and second tube flow passage openings directly between the electrodes.

* * * * *

UNITED STATES PATENT AND TRADEMARK OFFICE
CERTIFICATE OF CORRECTION

| | | |
|---|---|---|
| PATENT NO. | : 6,706,039 B2 | |
| DATED | : March 16, 2004 | |
| INVENTOR(S) | : Peter M. J. Mulier et al. | |

It is certified that error appears in the above-identified patent and that said Letters Patent is hereby corrected as shown below:

Column 10,
Lines 3-26, cancel beginning with "5. An apparatus to treat tissue in the presence of an" to and including "ratus." and insert the following claim:

> 5. The method of claim 1 wherein:
> the tissue comprises soft tissue.

Lines 27-29, cancel beginning with "6. The apparatus of claim 5, further comprising:" to and including "second tube." in column 10, line 29 and insert the following claim:

> 6. The method of claim 1 wherein:
> the electric current comprises radiofrequency alternating current provided from a radiofrequency generator.

Lines 30-54, cancel beginning with "7. An apparatus to treat tissue in the presence of an" to and including "passage openings, respectively, external the apparatus." and insert the following claim:

7. The method of claim 1 wherein:
the electrically conductive fluid is provided from a fluid source.

Lines 55-56, cancel beginning with "8. The apparatus of claim 7, wherein:" to and including "the separation device comprises a vacuum tube." and insert the following claim:

> 8. The method of claim 1 wherein: the electrically conductive fluid comprises an electrically conductive solution.

Line 59-column 11, cancel beginning with "10. An apparatus to treat tissue in the presence of an" to and including "passage openings, respectively, external the apparatus." Line 18 and insert the following claim:

> 10. An apparatus to treat tissue in the presence of an electrical current and an
electrically conductive fluid, the apparatus comprising:
a bipolar electrode configuration comprising a first electrode spaced from a second
> electrode, the first electrode and the second electrode both uncovered and
> configured to be exposed to and adjacent to the tissue;

UNITED STATES PATENT AND TRADEMARK OFFICE
CERTIFICATE OF CORRECTION

PATENT NO. : 6,706,039 B2
DATED : March 16, 2004
INVENTOR(S) : Peter M. J. Mulier et al.

It is certified that error appears in the above-identified patent and that said Letters Patent is hereby corrected as shown below:

the first electrode located at the distal end of a first tube, the first tube providing a first tube flow passage and a first tube flow passage opening, the first tube flow passage opening positioned to dispense the electrically conductive fluid adjacent the first electrode;
    the second electrode located at the distal end of a second tube, the second tube providing a second tube flow passage and a second tube flow passage opening, the second tube flow passage opening positioned to dispense the electrically conductive fluid adjacent the second electrode; and
    wherein the first fluid passage opening and the second fluid passage opening are arranged to facilitate a reduction in fluid interaction between the electrically conductive fluid dispensed from the first and second tube flow passage openings, respectively, external the apparatus.

Column 11,
Lines 32-37, cancel beginning with "15. The apparatus of claim 10 further comprising:" to and including "openings, respectively, external the apparatus." and insert the following claim:

15. The apparatus of claim 10 further comprising:
    a separation device to facilitate a reduction in fluid interaction between the electrically conductive fluid dispensed from the from the first and second tube flow passage openings, respectively, external the apparatus.

Lines 38-42, cancel beginning with "16. The apparatus of claim 10 further comprising:" to and including "electrical current directly between the electrodes." and insert the following claim:

16. The apparatus of claim 10 further comprising:
    a separation device to prevent electrically conductive fluid dispensed from the first and second tube flow passage openings from shorting electrical current directly between the electrodes.

Lines 43-47, cancel beginning with "17. The apparatus of claim 10 further comprising:" to and including "directly between the electrodes." and insert the following claim:

17. The apparatus of claim 10 further comprising:
    a separation device to prevent the migration of electrically conductive fluid dispensed from the first and second tube flow passage openings directly between the electrodes.

UNITED STATES PATENT AND TRADEMARK OFFICE
CERTIFICATE OF CORRECTION

PATENT NO. : 6,706,039 B2
DATED : March 16, 2004
INVENTOR(S) : Peter M. J. Mulier et al.

It is certified that error appears in the above-identified patent and that said Letters Patent is hereby corrected as shown below:

Column 12,
Lines 35-37, cancel beginning with "22. The apparatus of claim 18 wherein: the second tube is" to and including "conductive.", and insert the following claim:

>    22. The apparatus of claim 18 wherein:
>    the second tube is at least one of electrically insulated and electrically non-conductive.

Lines 38-42, cancel beginning with "23. The apparatus of claim 18 wherein:" to and including "trical current directly between the electrodes.", and insert the following claim:

>    23. The apparatus of claim 18 wherein:
>    the separation device prevents electrically conductive fluid dispensed from the first and second tube flow passage openings from shorting electrical current directly between the electrodes.

Lines 43-47, cancel beginning with "24. The apparatus of claim 18 wherein:" to and including "directly between the electrodes.", and insert the following claim:

>    24. The apparatus of claim 18 wherein:
>    The separation device prevents the migration of electrically conductive fluid dispensed from the first and second tube flow passage openings directly between the electrodes.

Signed and Sealed this

Seventeenth Day of August, 2004

JON W. DUDAS
*Acting Director of the United States Patent and Trademark Office*